United States Patent [19]

O'Boyle

[11] Patent Number: 4,917,687

[45] Date of Patent: * Apr. 17, 1990

[54] APPARATUS FOR CONTROLLING FLUID FLOW RATE

[75] Inventor: Matthew O'Boyle, Houston, Tex.

[73] Assignee: Sta-Set Corporation, Houston, Tex.

[*] Notice: The portion of the term of this patent subsequent to Apr. 18, 2006 has been disclaimed.

[21] Appl. No.: 305,190

[22] Filed: Feb. 1, 1989

Related U.S. Application Data

[63] Continuation of Ser. No. 938,620, Dec. 5, 1986, Pat. No. 4,822,344.

[51] Int. Cl.[4] .............................................. A61M 5/00
[52] U.S. Cl. ....................................... 604/248; 138/43
[58] Field of Search .................... 604/30, 32, 246, 248; 138/42–45; 251/118, 126, 127, 205, 208

[56] References Cited

U.S. PATENT DOCUMENTS

| 1,964,300 | 6/1934 | Perry et al. | |
| 2,236,084 | 3/1941 | Brown | |
| 2,323,115 | 6/1943 | Bryant | |
| 2,833,311 | 5/1958 | Baldelli | |
| 3,532,126 | 10/1970 | Boothe | |
| 3,532,127 | 10/1970 | Vogelsang et al. | |
| 3,877,428 | 3/1977 | Seagle et al. | |
| 4,011,893 | 3/1977 | Bentley | |
| 4,275,767 | 6/1981 | Westfall | |
| 4,298,000 | 11/1981 | Thill et al. | |
| 4,509,946 | 4/1985 | McFarlane | 604/246 |
| 4,552,178 | 11/1985 | Olsson | |
| 4,634,434 | 1/1987 | Marino et al. | 604/246 |
| 4,738,665 | 4/1988 | Shepard | 604/248 |
| 4,807,660 | 2/1989 | Aslanian | 604/32 |
| 4,822,344 | 4/1989 | O'Boyle | 604/248 |

FOREIGN PATENT DOCUMENTS

| 168675 | 1/1986 | European Pat. Off. |
| 2091189 | 5/1971 | France |

OTHER PUBLICATIONS

"Low-Compliance Perfusion Pump for Oesophagael Manometry", P. Ask, *Medical & Biological Engineering & Computing*, Nov. 1978, pp. 732–738, vol. 16.

*Primary Examiner*—Stephen C. Pellegrino
*Assistant Examiner*—Ralph Lewis
*Attorney, Agent, or Firm*—Fitch, Even, Tabin & Flannery

[57] ABSTRACT

A variable infusion device for administering liquids parenterally to a patient is formed of inexpensive plastic members. The device includes an elongated passage defined between two members of the device which are bonded to one another. A third member is movable relative to the first and second members to change the length of the elongated passage through which liquid flows thereby changing the flow rate of the liquid through the device. The liquid flow rates to the patient can be incrementally adjusted over a wide range of flow rates. Settings also include a flow rate for merely keeping the patient's vein open.

8 Claims, 9 Drawing Sheets

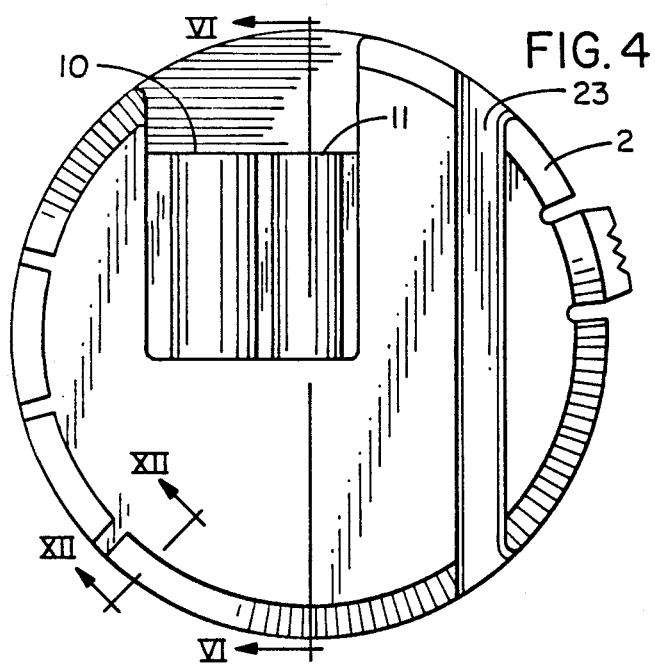
FIG. 4
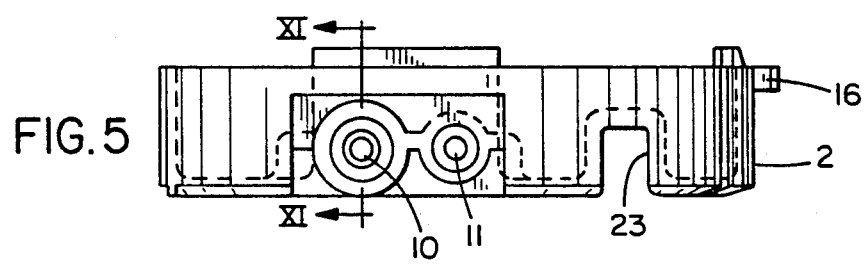
FIG. 5
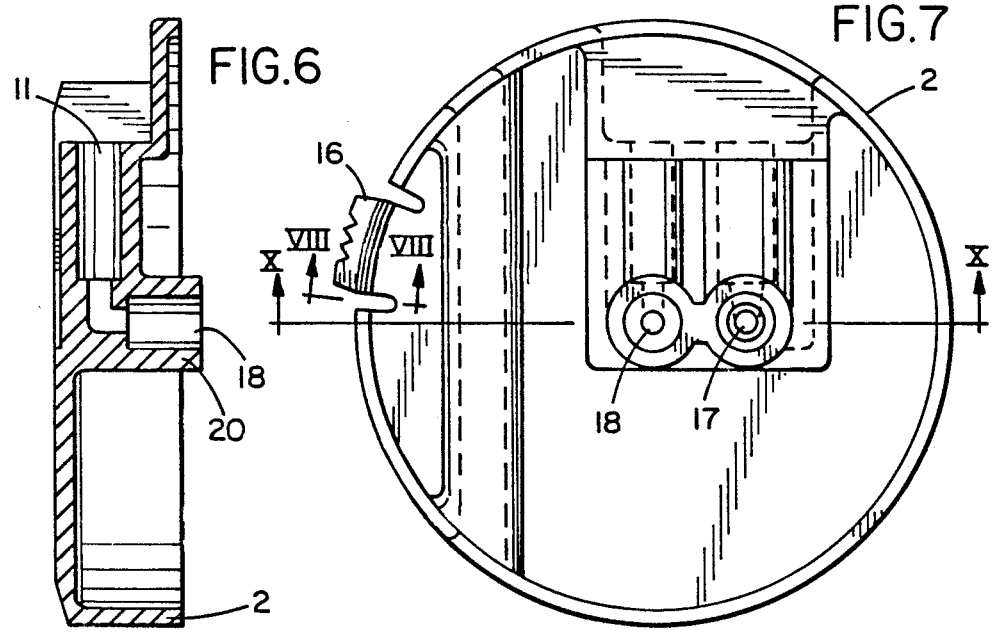
FIG. 6
FIG. 7

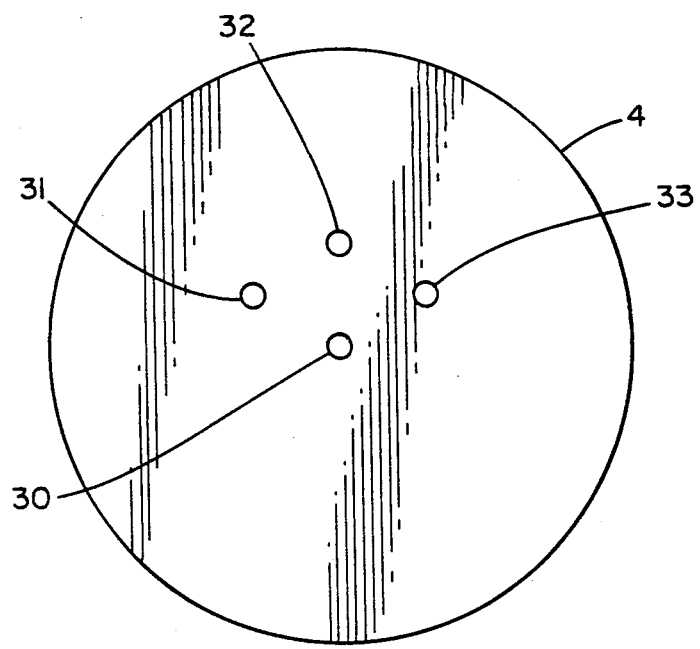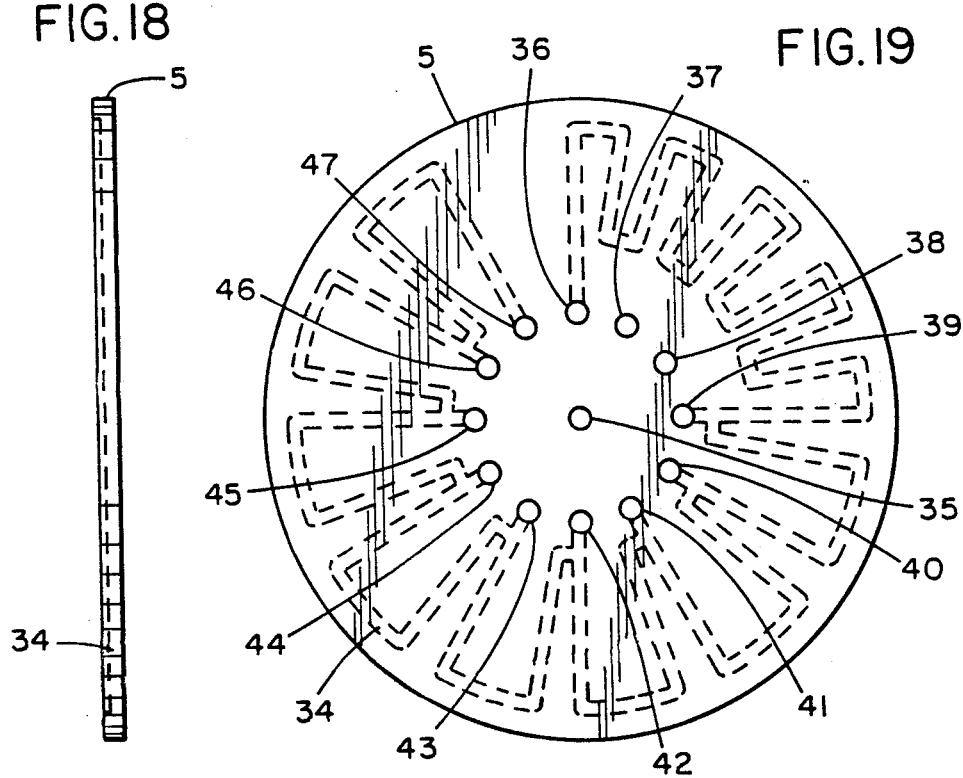

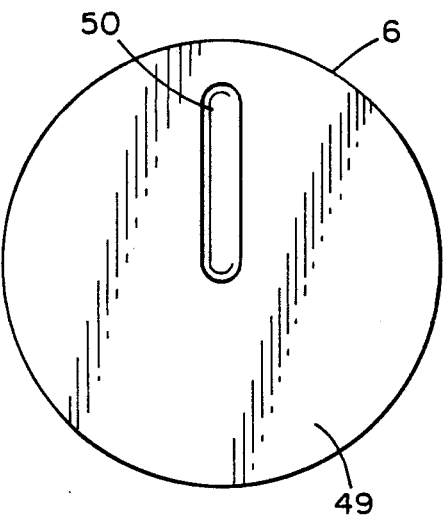
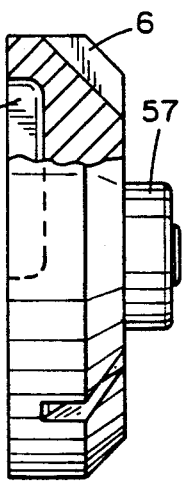
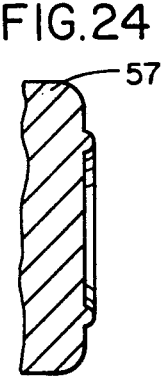
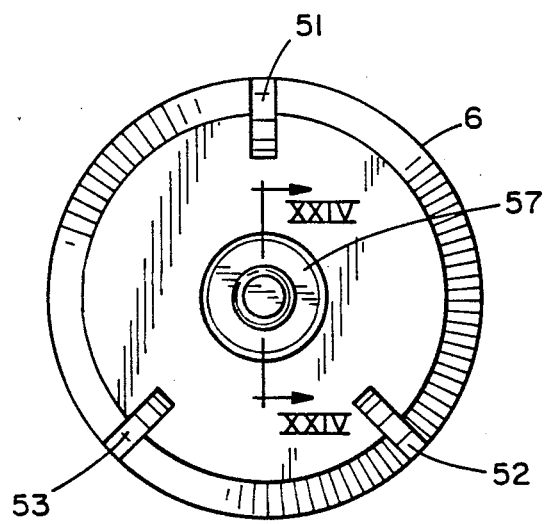
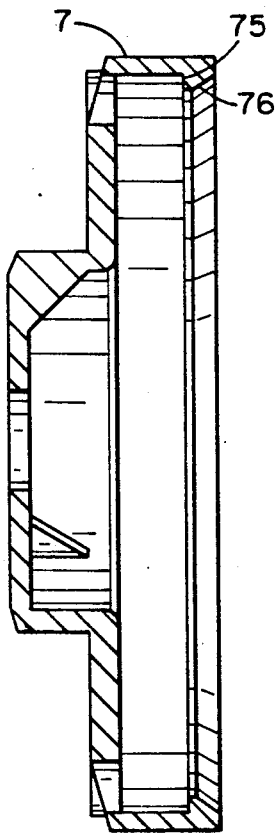

APPARATUS FOR CONTROLLING FLUID FLOW RATE

Tis is a continuation of application Ser. No. 938,620, filed Dec. 5, 1986, now U.S. Pat. No. 4,822,344.

BACKGROUND AND SUMMARY OF THE INVENTION

The present invention is directed to an apparatus for controlling fluid flow rate. More particularly, the invention relates to a variable infusion device for administering liquids parenterally to a patient.

The administration of liquids parenterally to a patient is a treatment that has been employed for many years. It typically involves the use of a container of liquid to be infused, an elongated flexible tube for conveying the liquid from the container to a patient and a cannula or catheter for insertion into the cardiovascular system of the patient to introduce the liquid for infusion into the patient's system. A variety of liquids may be infused in this manner, including dextrose, saline, Ringers solution, and water or any combinations of these solutions. Others include whole blood and plasma. More recently, drugs such as antibiotics, heparin, etc. are administered in this manner.

In past, the most common manner of controlling the flow of the liquid being administered to the patient has been to selectively collapse a portion of the flexible delivery tube using a roller clamp, for example. The rate of flow in such cases is determined by the rate at which drops of liquid are observed falling through a conventional drip chamber. While this arrangement for administering liquids parenterally has been satisfactory where the desired flow rates are comparatively fast and the accuracy of the flow rate is not crucial, it is not suitable where very accurate or very low flow rates are necessary as, for example, where a drug must be administered to a patient at a very low constant flow rate over an extended period of time or where a very low flow rate is desired merely to keep intravenous cannulas and catheters from becoming clogged with clotting blood until further administration of liquid medications is desired.

An object of the present invention is to provide a variable infusion device for administering liquid parenterally to a patient which avoids the aforementioned drawbacks of this known arrangement for controlling the flow of parenteral fluids to a patient. More particularly, an object of the invention is to provide a variable infusion device for administering liquids parenterally which may be placed at any point in a supply line between a container of liquid to be administered to a patient and the patient for accurately controlling the liquid flow rates over extended periods of time at a desired flow rate which may include very low flow rates.

A further object of the invention is to provide a variable infusion device for administering liquid parenterally to a patient which regulates the flow of liquid by selectively varying the effective length of the flow passage through the device.

An additional object of the invention is to provide a variable infusion device for administering liquid parenterally to a patient which can be manufactured at relatively low cost with a minimum number of parts for economical use in a wide variety of applications.

These and other objects of the invention are attained by the variable infusion device of the present invention which comprises means defining an elongated passage through which a liquid can be flowed, and means for changing the flow rate of a liquid flowing through the elongated passage. The means for changing the flow rate includes means for changing the length of the elongated passage through which the liquid is flowed thereby changing the flow rate of the liquid. The means defining an elongated passage includes a first member having an elongated groove with a small cross-sectional area formed in a surface thereof and a second member having a surface overlying the groove. The means for changing the length of the elongated passage through which the liquid is flowed comprises a third member having means for selectively bypassing the liquid about at least a portion of the elongated passage defined between the first and second members through a bypass passage. The first and second members are secured against movement relative to one another in the device. As a result, an effective liquid seal about the elongated passage between the first and second members can be maintained even in the case both members are formed of a plastic material, for example. According to the preferred embodiment, the first and second members are bonded to one another. The third member is formed of an elastomeric material which is pressed against a surface of one of the first and second members to form a liquid seal therewith, while permitting relative movement between the third member and the assembly of the first and second members for selectively bypassing the liquid about at least a portion of the elongated passage defined between the first and second members.

At least one of the first and second members has a plurality of spaced openings communicating with respective portions of the elongated passage defined between the first and second members. The third member is movable relative to the spaced openings to selectively communicate a bypass passage with respective ones of the openings to thereby change the length of the elongated passage through which liquid is flowed. The third member closes the other openings while communicating a selected one of the openings with the bypass passage. In the disclosed embodiment, the first, second and third members are retained within a dial cover of the device.

The disclosed variable infusion device also includes a fourth member having an additional elongated groove formed in a surface thereof. An additional surface of the second member overlies the additional groove. The second member is secured against movement relative to both the first and fourth members. In the preferred form of the invention, the second member is bonded to both the first and fourth members to form an assembly. The assembly is mounted upon a connector housing of the device via the fourth member. The connector housing is provided with an inlet and an outlet at the respective ends of the means defining an elongated passage for communicating liquid to for from the device. The second member of the device is preferably formed of a plastic material which is chemically bonded to the first and fourth These and other objects, features and advantages of the present invention will become apparent from the following description when taken in connection with the accompanying drawings which show, for purposes of illustration only, one embodiment in accordance with the invention.

BRIEF DESCRIPTION OF THE DRAWINGS

FIG. 4 is a front view of the outer side of the connector housing of the device of FIG. 1 which corresponds to the side of the device as shown in FIG. 3;

FIG. 5 is a top view of the connector housing shown in FIG. 4;

FIG. 6 is a sectional view of the connector housing taken along line VI—VI in FIG. 4;

FIG. 7 is a rear or back view of the inner side of the connector housing as shown in FIG. 4;

FIG. 16 is a front view of a baffle plate of the device shown in FIG. 1;

FIG. 17 is a side edge view of the baffle plate of FIG. 16;

FIG. 18 is a side edge view of another metering plate of the variable infusion device shown in FIG. 1;

FIG. 19 is a right side view of the metering plate of FIG. 1 illustrating in dashed lines a serpentine shaped groove formed in the back or left side of the plate as shown in FIG. 18 with a series of passages extending through the plate at intervals along a circle about the center of the plate where a passage is provided for communication with the outlet of the connector housing by way of corresponding passages in the baffle plate of FIGS. 16 and 17 and the metering plate of FIGS. 14 and 15;

FIG. 20 is an inner side view of a shunt of the variable infusion device shown in FIG. 1;

FIG. 21 is a sectional view of a portion of the shunt taken along the line XXI—XXI in FIG. 20 illustrating a groove in the shunt which forms a bypass passage with the surface of the adjacent metering plate in the assembled device;

FIG. 22 is a side elevational view, partially in a cross-section, of the shunt taken from the right side of FIG. 20;

FIG. 23 is of the back or outer side of the shunt as shown in FIG. 20;

FIG. 24 is a sectional view of a portion of the shunt taken along the line XXIV—XXIV in FIG. 23;

FIG. 28 is an enlarged cross-sectional view of the dial cover taken along the line XXVIII—XXVIII in FIG. 27.

DETAILED DESCRIPTION OF THE DISCLOSED EMBODIMENT

Figure 1:
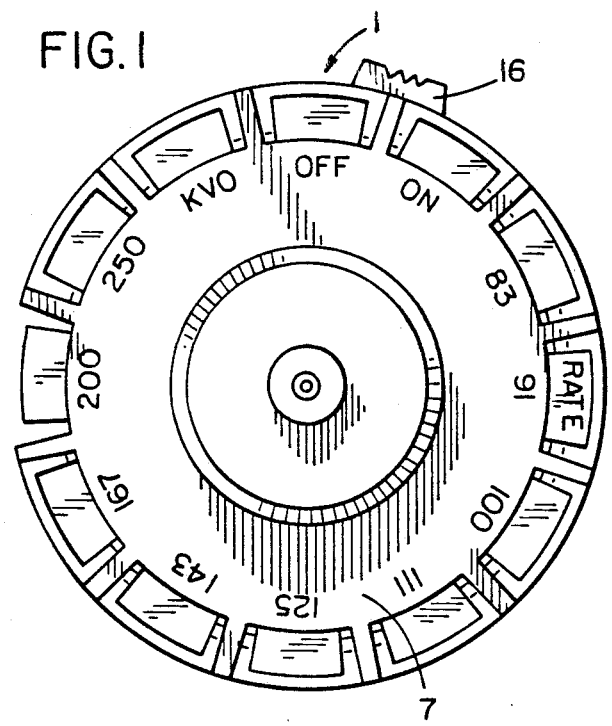
FIG. 1 is a front view of a variable infusion device according to a preferred embodiment of the invention.
Figure 2:
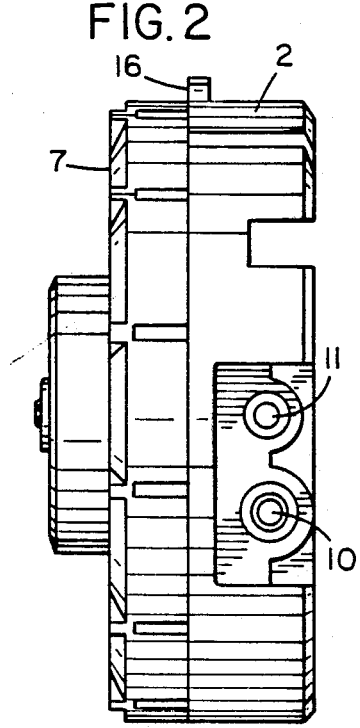
FIG. 2 is a side view from the right side of the variable infusion device shown in FIG. 1.
Figure 3:
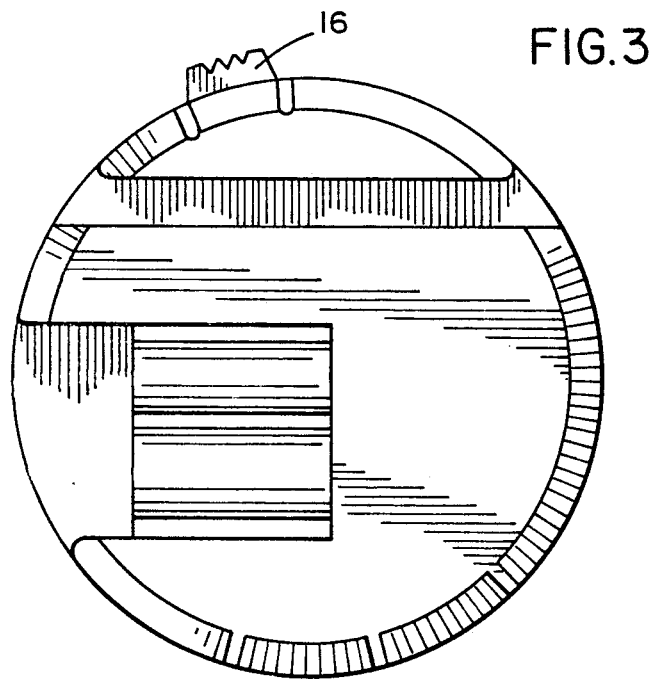
FIG. 3 is a rear or back view of the device illustrated in FIG. 1.
Figure 8:
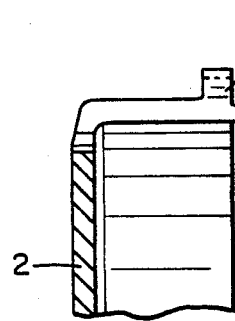
FIG. 8 is a sectional view of a portion of the connector housing taken along the line VIII—VIII in FIG. 7.

Referring now to the drawings, the variable infusion device 1 according to the preferred embodiment of the invention is formed of a connector housing 2, a KVO (keep vein open) metering plate or disc 3, a baffle plate 4, a metering plate 5, a shunt 6 and a dial cover 7. These components are assembled as shown in FIGS. 1–3, 13 and 29 to form the variable infusion device 1.

The device is useful for administering liquids parenterally to a patient. The Poiseuille equation defines the relationship between the length and diameter of a tube and the fully developed laminar flow rate of a fluid through the tube. The variable infusion device 1 of the invention operates in accordance with this relationship in that the length of the elongated liquid passage through the device can be incrementally varied, so that a series of predetermined liquid flow rates can be achieved. When the device is used in the manner illustrated in FIG. 29, liquid from an IV solution plastic bag 8 passes through a clear drip chamber 9 to the inlet 10 of the device 1, then flows through an elongated passage in the device 1 and exits from the device through an outlet 11. It is then conveyed to a patient 13 through a clear plastic tube 12 by way of a connector 14 and a needle set 15. See FIGS. 2, 3 and 29. The length of the elongated passage through the device 1 can not only be incrementally varied to adjust the flow rate of the liquid through the device and to the patient, but also the passage can be completely closed or blocked in the device 1 to stop the flow or completely opened to provide unrestricted flow.

Adjustments in the flow rate are made by rotating the assembly of dial cover 7 and shunt 6 of the device relative to a connector housing and a sub-assembly of metering plates and a baffle plate which is non-rotatably secured to the connector housing. Any one of twelve different settings, shown on the dial cover 7 in FIG. 1, can be selected by the operator by moving the desired indicium on the dial cover to a position relative to an indicating and alignment tab 16 formed on the connector housing 2. Namely, the possible positions include: an OFF position where no flow is permitted through the device 1; an ON position which provides a short, relatively large cross-sectional area passage for relatively unrestricted flow of liquid through the device; and a series of nine numerically labelled positions which can be individually selected to incrementally vary the flow rate through the device 1 from, for example, 83 milliliters per hour to 250 milliliters per hour, as illustrated on the dial cover 7 in FIG. 1; The plurality of respective flow rates are attained because the rotation of the dial cover 7 to position the respective indicia thereon relative to the tab 16 results in incremental changes in the effective length of the elongated passage for the liquid flowing through the device. Alignment of the KVO dial position with the tab 16 causes the liquid to flow through a lengthy passage within the device 1 to restrict the flow rate to only a few milliliters per hour. This amount corresponds to that necessary to keep the patient's vein open while administering only a minimum of liquid parenterally to the patient. The liquid administered with the device 1 can be any liquid suitable for parenteral administration, including dextrose, saline, Ringers solution, and water or any combination of these solutions. Drugs such as antibiotics, heparin, etc., can also be administered as will be readily apparent to the skilled artisan.

The connector housing 2 is formed with the inlet 10 and outlet 11 located on the outer side thereof. Passages 17 and 18 extend from the inlet 10 and outlet 11, respectively, through the connector housing to respective female fittings 19 and 20. The outlet passage 18 is coaxial with the center of the circular connector housing 2 at the fitting 20.

Figure 9:
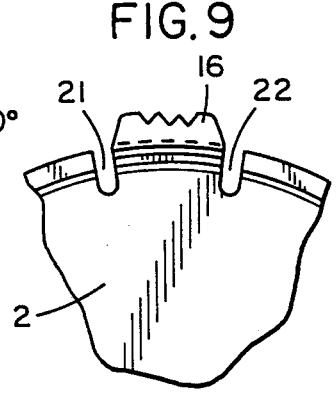
FIG. 9 is an enlarged top view of indicating an alignment tab of the connector housing taken from the right side of FIG. 8.
Figure 12:
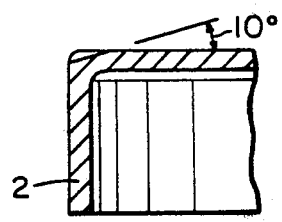
FIG. 12 is a sectional view of a portion of the connector housing taken along the line XII—XII in FIG. 4.
Figure 10:
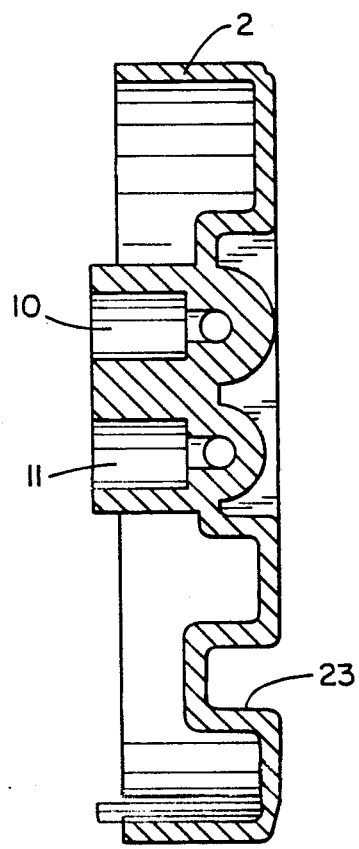
FIG. 10 is a sectional view of the connector housing taken along the line X—X in FIG. 7 and showing the inlet and outlet of the device of FIG. 1 in cross-section.
Figure 11:
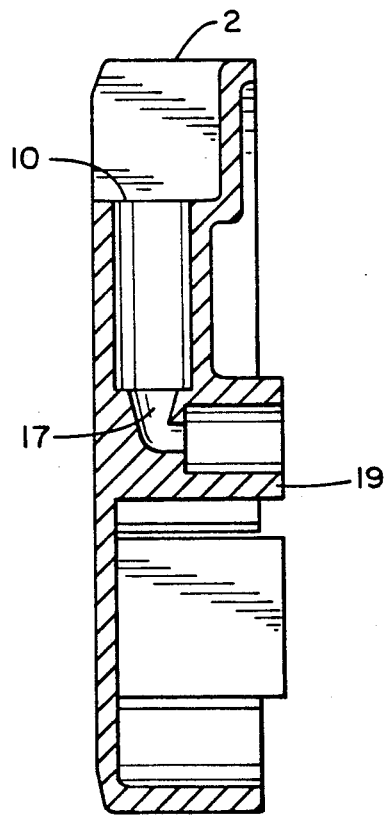
FIG. 11 is a sectional view of the connector housing taken along the line XI—XI in FIG. 5.
Figure 29:
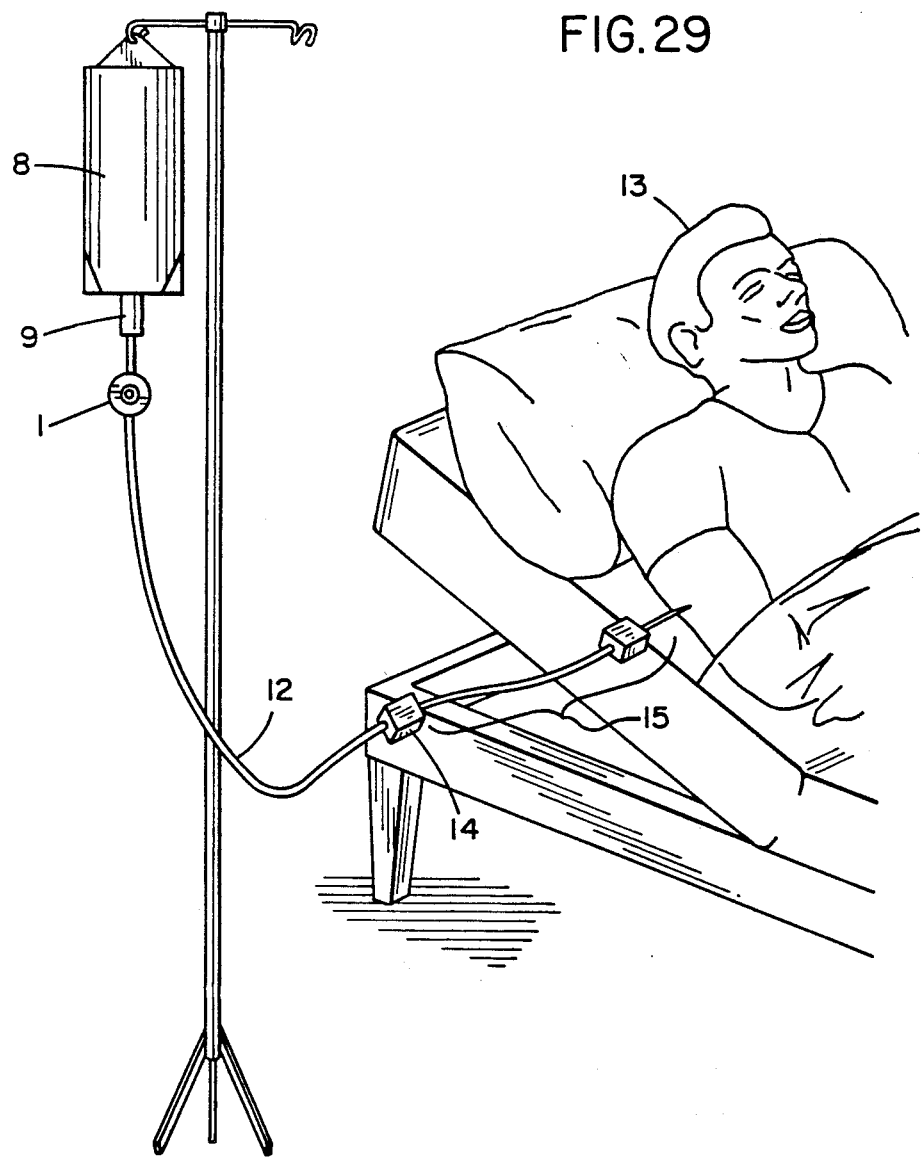
FIG. 29 is a schematic drawing illustrating the variable infusion device of FIG. 1 and used in the flow line for controlling the flow of an IV solution from an IV solution bag to a patient.

The indicating and alignment tab 16 is integrally formed with the connector housing 2. Grooves 21 and 22 are formed in the housing on opposite sides of the tab 16 as shown in FIG. 9. The outer free end of the tab 16 projects axially outward from the inner side of the connector housing for cooperation with the dial cover 7. A channel 23 is formed in the outer side of the connector housing 2. The channel can be used to guide the clear plastic IV tube 12 connected to the outlet 11 of the device. A similar tube is connected to the inlet 10 through an appropriate fitting for conveying liquid to the device 1. Alternatively, as shown in FIG. 29, a clear drip chamber can be connected directly to the inlet 10. The connector housing 2 is preferably integrally formed of a plastic material as by molding. One suitable material is rigid polyvinylchloride or polycarbonate. The outside surfaces of the connector housing are preferably polished so as to be smooth to the touch when adjusting the flow rate with the device 1. The diameter of the passages 17 and 18 in the connector housing 2 can be $\frac{1}{8}$ inch and 5/32 inch, respectively, for example, so as not to offer any substantial resistance to the flow of liquid therethrough.

Figure 13:
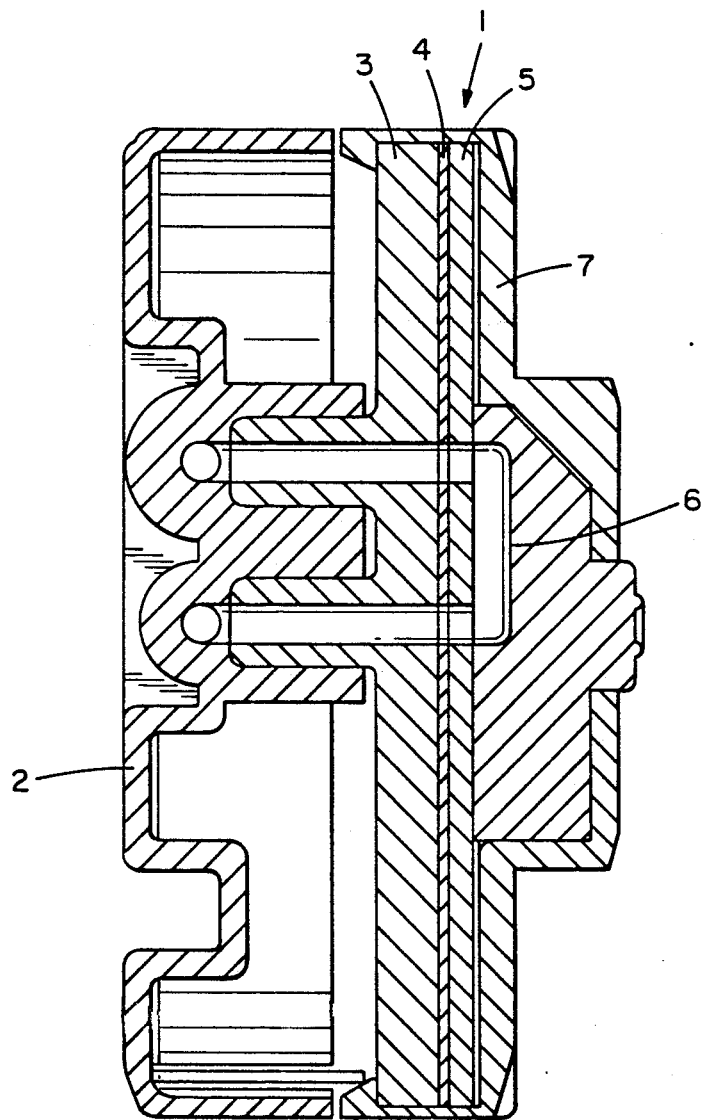
FIG. 13 is a sectional view through the center of the assembled device of FIG. 1 with the dial in the ON position.

The KVO metering plate 3 is in the form of a circular disc or plate having projections 24 and 25 formed integrally therewith on one side of the plate 3. The projections are adapted to mate with the respective female fittings 19 and 20 of the connector housing 2 in the assembled condition as shown in FIG. 13. The projections 24 and 25 are formed with passages 26 and 27 therethrough for alignment with the passages 17 and 18 in the connector housing 2 at one end thereof. The passages extend through the metering plate 3 from the projections 24 and 25 to the opposite side of the metering plate. The passage 27 for the outgoing liquid flow is coaxial with the center of the metering plate 3.

Figure 15:
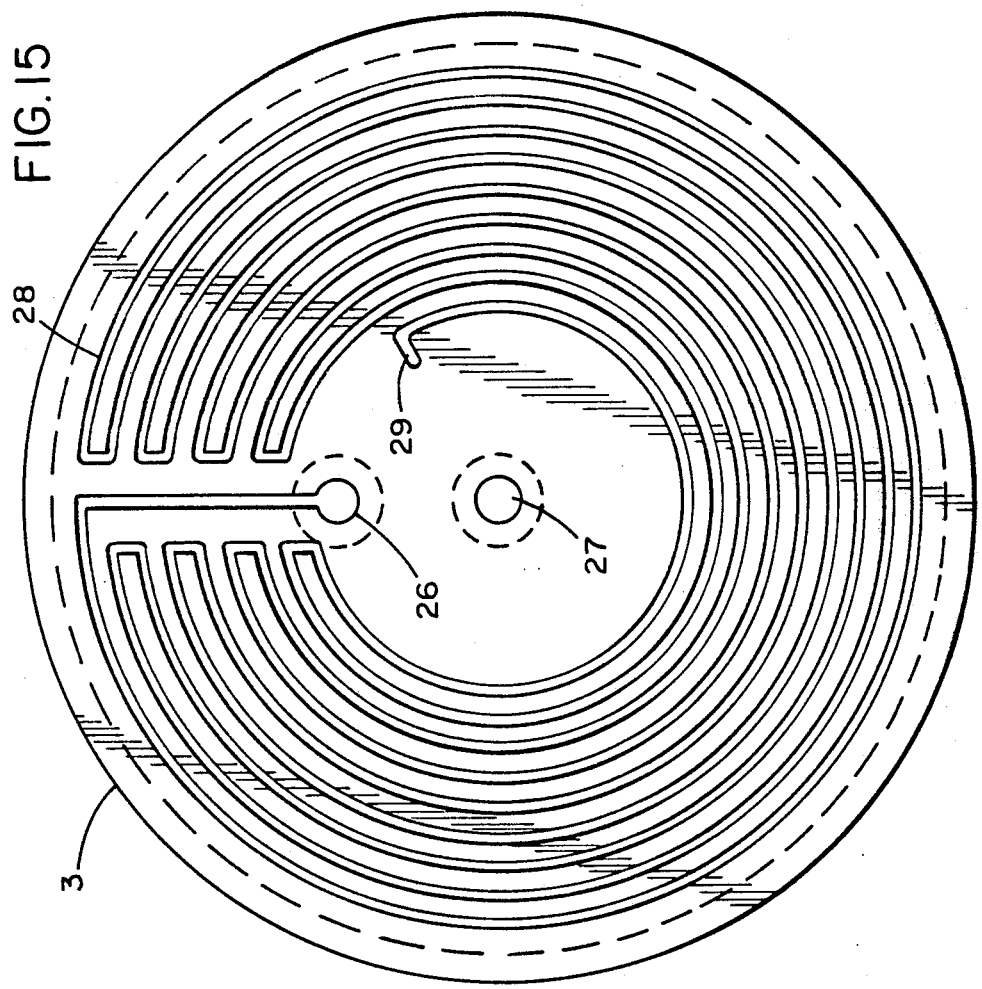
FIG. 15 is a right side view of the metering plate shown in FIG. 14 illustrating an elongated groove formed in the surface of the plate and extending from the passage in communication with the inlet in an array of concentric convolutions to an inner end spaced from the passage in the plate communicating with the outlet in the connector housing and along the same radius of curvature as the passage in the plate communicating with the inlet.
Figure 14:
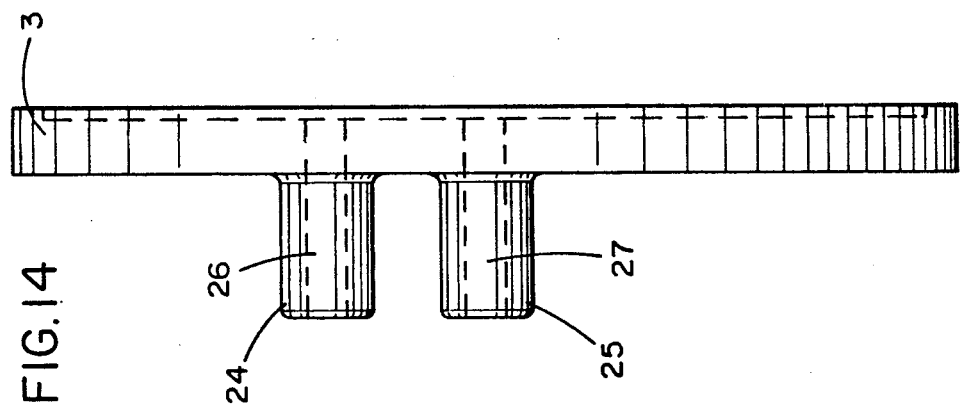
FIG. 14 is an edge side view of one metering plate of the device of FIG. 1 an illustrating two projections provided on the plate having passages extending therethrough for communicating with the inlet and outlet of the connector housing.
Figure 25:
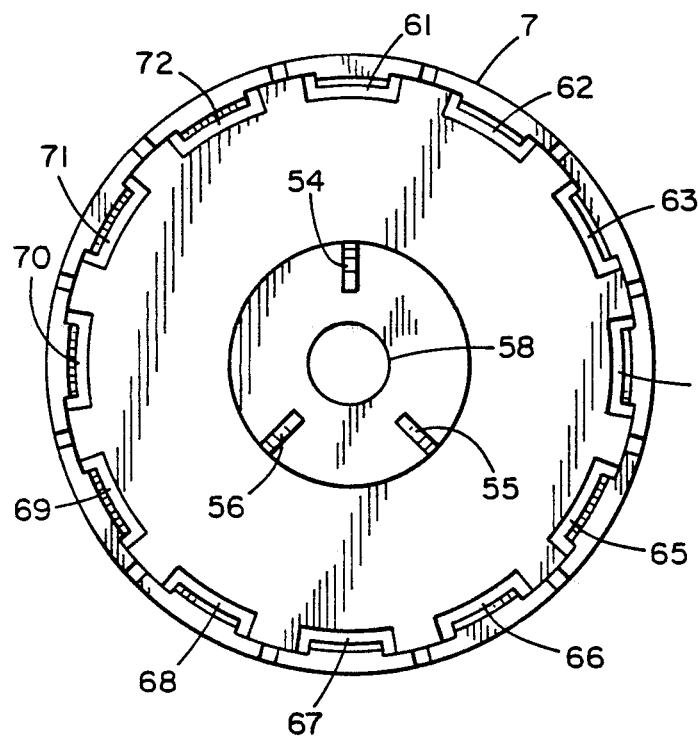
FIG. 25 is an inner side view of the dial cover of the variable infusion device of FIG. 1.
Figure 26:
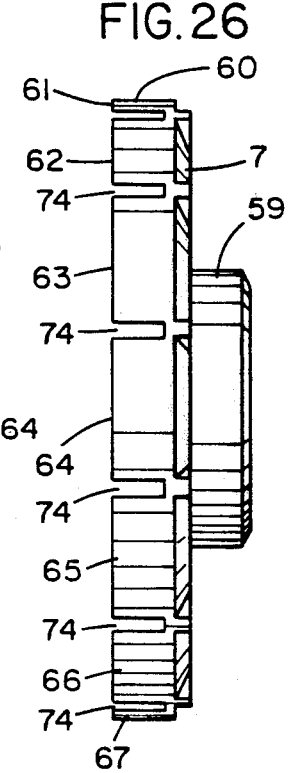
FIG. 26 is an edge side view of the dial cover taken from the right side of FIG. 25.
Figure 27:
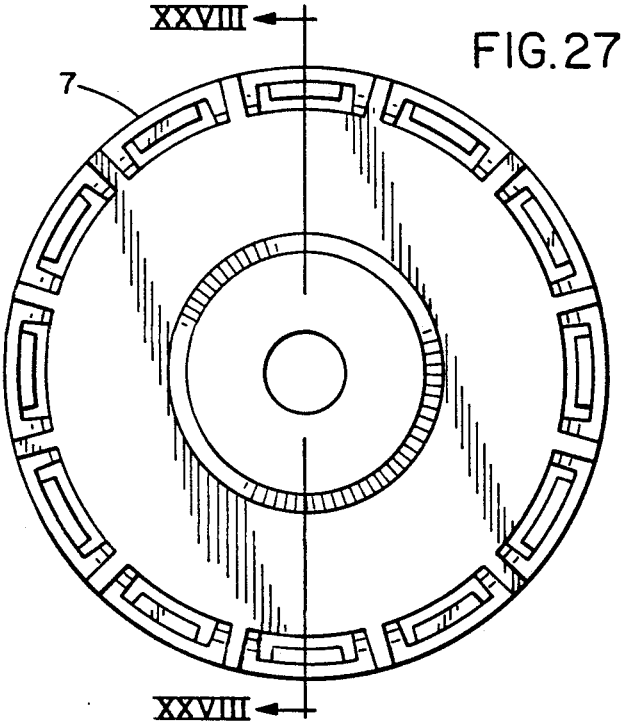
FIG. 27 is a view of the back or outer side of the dial cover as shown in FIG. 25.

The side of the metering plate 3 opposite the projections 24 and 25 is formed with an elongated groove 28 which extends from the passage 26 in an array of concentric convolutions to an inner end 29 spaced from the passage 26 along the same radius of curvature as the passage 26 with respect to the central axis of the plate 3 extending through the center of the passage 27. Particularly, the inner end 29 is spaced an angle of 60° from the passage 26 as shown in FIG. 15. The groove 28 has a substantially smaller cross-sectional area than the passage 26 communicating therewith. For example, the groove 29 can have a semi-circular shape as seen in cross-section with the radius thereof being less than 0.015 inch. The small size of the groove 29 and the considerable length thereof serve to reduce the flow of the liquid therein to only a few milliliters per hour. This amount is sufficient to keep a patient's vein open while minimizing the volume of liquid administered. In the illustrated embodiment the pitch between the adjacent circular segments of the groove 29 is 0.048 inch. The passage 26 and the inner end 29 of the groove 28 are located on a circle about the passage 27 having a diameter of 0.500 inch in the illustrated embodiment. The surface of metering plate 3 with the elongated groove 28 formed therein is flat with 0.002 inch T.I.R. and has a non-reflective finish. The opposite surface of the plate is polished. The plate is preferably formed of a molded plastic material such as polysulfone plastic.

The baffle plate 4 of the device 1 as shown in FIGS. 16 and 17 is a thin, flat circular member with the same outer diameter as the metering plate 3, for example, 1.502 inches. The plate 4 is formed with four through passages 30–33 as shown in FIG. 16. Each of the passages has a diameter of 0.060 inch, which corresponds to the diameter of the passages 26 and 27 in the metering plate 3. The passage 30 extends along the center axis of the circular plate 4 for axial alignment with the passage 27 of the plate 3 in the assembled condition as shown in FIG. 13. The three passages 31, 32 and 33 are spaced 60° from one another about a circle having its center through the central axis of the plate 4 and having a diameter of 0.500 inch. The middle passage 32 of the three passages is adapted to be aligned with the passage 26 in the KVO metering plate 3 in the assembled condition shown in FIG. 13. One of the other passages 31 and 33 is coincident with the inner end 29 of the elongated groove 28 in the metering plate 3 in the device 1. The two passages 31 and 33 are symmetrically positioned with respect to a center line of the baffle plate 4 passing through the passages 30 and 32 as shown in FIG. 16, so that the device 1 will be operable even if the plate 4 is turned 180° about this center line during assembly.

The baffle plate 4 has a thickness of 0.015 inch in the illustrated embodiment. The plate 4 is formed of a plastic material which can be chemically bonded at its respective surfaces to the adjacent metering plates 3 and 5. Preferably, the baffle plate 4 is formed of a polysulfone plastic material such as a Union Carbide Udel P1700 grade. The assembly of the metering plate 3, baffle plate 4 and metering plate 5 are chemically bonded to one another by immersing plate 4 in cyclohexanone solvent and then welding or bonding the three members together under the application of pressure. In the assembled condition, the metering plates 3 and 5 and intermediate baffle plate 4 are secured against movement relative to one another as a result of their bonded surfaces. Further, the baffle plate 4 which is bonded to the metering plates 3 and 5 forms a liquid tight seal against the surfaces of the metering plates to close the elongated grooves formed in the surfaces of the plates and thereby form elongated passages with the grooves of the metering phases for the flow of liquid through the device.

The metering plate 5 is shown in detail in FIGS. 18 and 19. The plate 5 is a thin, flat circular member which, in the illustrated embodiment has a thickness of 0.040 inch and a diameter of 1.504 inch. It is preferably formed of molded polysulphone, the same plastic used for the metering plate 3 and baffle plate 4. A serpentine-shaped groove 34 is formed in one surface of the metering plate 5 as shown in FIGS. 18 and 19. The groove may have a width of 0.025 inch and a depth of a 0.015 inch, for example, and extends in serpentine fashion completely around the circular plate 5. A central through hole 35 is formed in the metering plate 5. The hole 35 has a diameter of 0.060 inch and is adapted to be aligned with the corresponding holes in the baffle plate 4, KVO metering plate 3 and connector housing 2 as illustrated in FIG. 13.

Twelve, equally spaced through holes or passages 36–47 are also formed in the metering plate 5 along a circle about the center of the circular plate. The hole 36 has a diameter of 0.060 inch. It communicates with one end of the serpentine-shaped groove 34 and is adapted to be aligned with the passage 32 in the baffle plate 4 and cooperating passages in the KVO metering plate 3 and connector housing 2 as illustrated in FIG. 13 of the drawings. The other eleven holes 37–47 are spaced every 30° about a circle having a diameter of 0.500 inch. The holes 37–47 have a diameter of 0.040 inch. There is no hole in the adjacent baffle plate 4 adapted to be aligned with the hole 37 in the metering plate 5 in order to provide an OFF position to interrupt flow through the device as discussed hereinafter. The hole or passage 38 in the assembled condition of the device is coincident with one of the passages 31 and 33 in the baffle plate 4 which in turn communicates with the end of the elongated groove 28 in the KVO metering plate 3. Passages 39–47 are each communicated with respective portions of the serpentine-shaped groove 34 for incrementally changing the length of the groove 34 through which liquid is flowed and thereby changing the flow rate through the device as discussed more fully hereinafter. Both sides of the metering plate 5 are flat within 0.002 T.I.R. The surface of the metering plate 5 having groove 34 formed therein is molded against a flat polished surface so that it has no flash projecting beyond the surface. The baffle plate 4 overlies the surface of the metering plate 5 having the groove 34 formed therein to form an elongated passage with the groove and surrounding plate 5. The baffle plate 4 is chemically bonded to the metering plate 5 as well as the KVO metering plate 3 in a fluid type manner, so as to effectively seal the elongated passages against leakage. The surface of the metering plate 5 opposite that having the groove 34 formed therein is flat and polished, so that the parting line formed thereon during the molding of the plate is flat with the surrounding surface to within 0.002 T.I.R. This surface of the plate 5 is adapted to be engaged in sealing, sliding relationship with the shunt 6 in the assembled condition of the device depicted in FIG. 13.

The shunt 6 shown in FIGS. 20–24 is a circular-shaped member having a diameter of 0.684 inch. The shunt is formed of an elastomeric material such as a synthetic rubber, by molding. The surface 49 thereof shown in FIGS. 20–22 is molded against a flat polished surface, so that it is sufficiently flat to form a seal against the adjacent surface of the metering plate 5 in the assembled condition of the device 1. The surface 49 of the shunt 6 is formed with a groove 50 therein. The depth of the groove is 0.050 inch. The bottom of the groove is rounded as shown in FIG. 21. The groove 50 and the cooperating surface of the metering plate 5 in the assembled condition form a passage for liquid flow from a selected one of the openings 37 and 39–48 in the adjacent metering plate 5, to the through hole 36 in the plate 5 in the direction of the outlet 11 of the device 1. The side of the shunt 6 opposite the surface 49 is formed with three grooves 51, 52 and 53 for receiving cooperating projections 54, 55 and 56 on the dial cover 7 in the assembled condition to prevent relative rotation between the dial cover and shunt. A central button 57 on the shunt 6 is adapted to project through a corresponding opening 58 in the dial cover 7. The button 57 of the shunt 6 serves as a distal septum (injection site). A protector cap (not shown) is provided over the button. When the patient needs an intravenous injection of a drug the hypodermic needle may be inserted through button 57 and the drug injected directly into the outlet channel of the device 1 for flowing directly to the patient. This avoids the need to make lots of punctures in the patient's limited number of intravenous injection sites.

Dial cover 7 is shown in detail in FIGS. 25–28. The dial cover is integrally formed of a plastic material as by molding. The same plastic material used to form the connector housing 2 can be used to form the dial cover. The dial cover 7 is circular in shape and is formed on one side with an annular projecting portion 59 having a central opening 58 therein for receiving the button 57 of the shunt 6. The opposite side of the dial cover is formed with a depending flange 60 formed of twelve axially projecting flange portions 61–73 which are spaced from one another by axially extending slots 74. The slots permit the flange portions 61–73 to be deflected slightly during adjustment of the device 1 by interaction with the indicating and alignment tab 16 of the connector housing. The outer, free end portions of the flange portions 61–73 each include a radially inwardly protruding portion 75 having a surface 76 inclined at an angle of 30° with respect to the central axis of the dial cover. The indicating and alignment tab 16 of the connector housing cooperates with the respective inclined surfaces 76 for accurately positioning the dial cover and shunt 6 associated therewith with respect to the assembly of the metering plate 5, baffle plate 4 and KVO metering plate 3 which is non-rotatably positioned in the connector housing 2. The projections 54, 55 and 56 on the dial cover are received within grooves 51, 52 and 53 in the shunt as noted above, so that the shunt rotates with the dial cover during adjustment of the device 1.

The bonded assembly of the KVO metering plate 3, baffle plate 4 and metering plate 5 is dimensioned to fit within the annular space defined by the depending flange 60 of the dial cover 7. To assemble the dial cover and the bonded assembly of the metering plates, the metering plates are snap-fitted into position against the bias of the individual depending flange portions 61–73 in cooperation with the inclined surfaces 76 thereon. The radially inwardly protruding portions 75 of the flanges 61–73 retain the assembly of the metering plates and baffle plate in position within the dial cover 7. The depth of the projecting portion 59 of the dial cover which receives the shunt 6 is slightly less than the height of the shunt 6, so that in the assembled condition of the device the shunt is compressed against the surface of the metering plate 5 to form a liquid seal therewith while permitting relative rotation of the shunt with respect to the surface of the metering plate 5 during adjustment of the variable infusion device 1. The projections 24 and 25 on the KVO metering plate 3 are received within the female fittings 19 and 20 of the connector housing and connected thereto as by solvent bonding to prevent relative rotation of the connector housing and the assembly of the metering plates and baffle plate.

During use of the variable infusion device 1, the valve cover 7 can be rotated with respect to the assembly of the metering plates and baffle plate and the associated connector housing to one of twelve different positions as indicated on the dial cover. In the OFF position, the groove 50 of the shunt 6 is aligned with passage 37 in the metering plate 5 and thus, passages within the device by the baffle plate 4, so that liquid flow through the device is interrupted. In the ON position a short, relatively large cross-sectional passage for liquid flow through the device 1 is provided by way of the inlet 10, passage 17 in the connector housing 2, passage 26 in metering plate 3, passage 32 in the baffle plate 4, passage 36 in the metering plate 5, groove 50 in the shunt 6, central passage 35 in metering plate 5, passage 30 in the center of baffle plate 4, passage 27 in the KVO metering plate 3 and passage 18 in the connector housing 2 to the outlet 18. This provides a relatively unrestricted flow path for a liquid, so as not to appreciably change the outgoing flow rate of the device 1 as compared with the incoming flow rate to the device.

When the variable infusion device 1 is adjusted to the setting KVO, the liquid flow is directed through the complete length of the elongated passage formed between the KVO metering plate 3 and baffle plate 4 in the elongated groove 28 and then through one of the passages 31 and 33 of the baffle plate 4, passage 38 in the metering plate 5, groove 50 of the shunt 6 and on to the outlet 18 in the same manner as described with respect to the ON position. Since the cross-sectional area of the elongated passage defined between the KVO metering plate 3 and baffle plate 4 is relatively small in comparison with the passages in the device leading to and from the elongated passage, and the length of this elongated passage is relatively long, the flow rate through the device 1 is relatively small, only a few milliliters per hour or that necessary to keep the patient's vein open while minimizing the quantity of liquid infused.

The other nine settings of the dial cover 7 result in liquid flow through the elongated passage defined between the baffle plate 4 and the metering plate 5 in the serpentine-shaped groove 34. In particular, each setting corresponds to a different length of the elongated passage defined by the serpentine-shaped groove 34 and the baffle plate 4 thereby incrementally change the flow rate depending upon the selected setting by changing the length of the elongated passage through which the liquid is flowed in the device 1. Thus, for example, as indicated on the dial cover in FIG. 1, the flow rate can be varied incrementally from 83 milliliters per hour to 250 milliliters per hour. Thus, the variable infusion device 1 of the invention permits the accurate control of the flow rate of the IV solution from the plastic bag 8 shown in FIG. 29 to the patient 13. The use of a relatively small number of components in the device 1, all of which may be formed of plastic, also results in a relatively low cost and easily manufactured variable infusion device.

While I have shown and described only one embodiment in accordance with the invention, it is understood that the same is not limited thereto, but is susceptible to numerous changes and modifications as known to those skilled in the art. For example, the variable infusion device of the invention could be formed without the KVO elongated passage between the metering plate 3 and baffle plate 4. An incremental adjustment of the flow rate through such a device would be based solely on changing the length of the elongated passage defined by the groove in the metering plate 5 and the adjacent baffle plate 4 through movement of the shunt 6 relative to the assembly of the metering plate and baffle plate. Therefore, I do not wish to be limited to the details shown and described herein, but intend to cover all such changes and modifications as are encompassed by the scope of the appended claims.

I claim:

1. Apparatus for controlling a flow rate of a liquid to be administered parenterally to a patent, said apparatus comprising:

a housing having spaced inlet and outlet channels for said liquid;

a first metering plate held against movement with respect to said housing, said plate having a front surface facing away from said housing and a rear surface facing said housing with a plurality of apertures extending between said front and rear surfaces, a first of said apertures being aligned with said inlet channel and a second of said apertures being aligned with said outlet channel;

plate means held against movement with respect to said housing and engaging the rear surface of said metering plate, said plate means having a first hole aligned with said inlet channel and said first aperture and a second hole aligned with said outlet channel and said second aperture, said rear surface of said metering plate and said plate means defining a first metering passage, one end of said passage communicating with one of said first and second apertures, the other end of said passage communicating with a third of said apertures, said plurality of apertures further comprising a series of apertures each of which communicates with said metering passage at spaced locations intermediate said ends; and cover means supported by said housing and movable relative thereto, said cover means having an interior surface engaging the front surface of said metering plate, said interior surface having a groove one end of which is continually in alignment with the other of said first and said second apertures, said cover means being movable with respect to said housing selectively to bring the other end of said groove into alignment with any predetermined one of said series of apertures and said third aperture whereby movement of said cover means with respect to said housing incrementally changes the flow rate of said liquid between said channels by adding or bypassing portions of said metering passage through which said liquid must travel in flowing from said inlet channel to said outlet channel.

2. Apparatus for controlling a flow rate as set forth in claim 1 wherein said plate means comprises a baffle plate and a second metering plate, said baffle plate being held between said first and second metering plates, said baffle plate and said second metering plate defining a second metering passage, one end of said second metering passage communicating with said one of said first and second apertures, said first metering plate having an additional aperture extending between said front and read surfaces and said baffle plate having an additional hole aligned with said additional aperture and the other end of said second metering passage, said cover means being movable with respect to said housing to bring the other end of said groove into alignment with said additional aperture whereby the first metering passage is bypassed and said liquid must traverse said second metering passage in flowing from said inlet channel to said outlet channel.

3. Apparatus for controlling a flow rate as set forth in claim 2 wherein said second metering passage is configured to provide a lesser flow rate than the entirety of said first metering passage.

4. Apparatus for controlling a flow rate as set forth in claim 2 wherein said first and second metering plates and said baffle plate are bonded together.

5. Apparatus for controlling a flow rate as set forth in claim 1 wherein the rear surface of said first metering plate is substantially flat and has a metering groove, said metering groove and the facing surface of said plate means defining said first metering passage.

6. Apparatus for controlling flow rate as set forth in claim 5 wherein said metering groove is serpentine-shaped.

7. Apparatus for controlling a flow rate as set forth in claim 1 wherein said cover means is rotatably mounted with respect to said housing, said other of said first and second apertures being disposed along the axis of rotation of said cover means.

8. Apparatus for controlling a flow rate as set forth in claim 7 wherein the remaining apertures apart from said other aperture are arranged in a generally circular array about said other aperture.

* * * * *

UNITED STATES PATENT AND TRADEMARK OFFICE
CERTIFICATE OF CORRECTION

PATENT NO. : 4,917,687

DATED : April 17, 1990

INVENTOR(S) : Matthew O'Boyle

It is certified that error appears in the above-identified patent and that said Letters Patent is hereby corrected as shown below:

Column 2, line 59, change "for" to --and--.

Column 2, line 62, after "fourth" insert --members--.

Column 3, line 34, change "an" to --and--.

Column 5, line 6, after "FIG. 1" change the semicolon to a period.

Column 7, line 8, change "polysulphone" to --polysulfone--.

Column 7, line 12, after "of" delete "a".

Column 7, line 43, after "device" insert --1--.

Column 10, line 22, change "patent" to --patient--.

Column 11, line 6, change "read" to --rear--.

Signed and Sealed this

Twenty-second Day of October, 1991

Attest:

HARRY F. MANBECK, JR.

*Attesting Officer*  *Commissioner of Patents and Trademarks*